United States Patent
Schutt et al.

(10) Patent No.: US 7,858,031 B2
(45) Date of Patent: Dec. 28, 2010

(54) VIAL PRESENCE INDICATOR FOR VIAL-BEARING RACK

(75) Inventors: Alexander Schutt, Engelsbrand (DE); Martin Trump, Pforzheim (DE)

(73) Assignees: Siemens Healthcare Diagnostics Inc., Tarrytown, NY (US); STRATEC Biomedical Systems AG, Birkenfeld-Graefenhausen (DE)

( * ) Notice: Subject to any disclaimer, the term of this patent is extended or adjusted under 35 U.S.C. 154(b) by 678 days.

(21) Appl. No.: 11/597,220

(22) PCT Filed: May 24, 2005

(86) PCT No.: PCT/US2005/018217

§ 371 (c)(1),
(2), (4) Date: Oct. 30, 2007

(87) PCT Pub. No.: WO2005/116613

PCT Pub. Date: Dec. 8, 2005

(65) Prior Publication Data

US 2008/0131328 A1    Jun. 5, 2008

Related U.S. Application Data

(60) Provisional application No. 60/574,000, filed on May 24, 2004.

(51) Int. Cl.
*B01L 3/02* (2006.01)
*B01L 99/00* (2010.01)

(52) U.S. Cl. ............... 422/63; 422/64; 422/65; 422/68.1; 422/100; 422/101; 422/102; 436/43; 73/863

(58) Field of Classification Search .............. 422/63, 422/64, 65, 100, 101, 68.1; 73/863; 436/43
See application file for complete search history.

(56) References Cited

U.S. PATENT DOCUMENTS

| 4,004,883 | A | | 1/1977 | Meyer et al. |
| 4,609,017 | A | * | 9/1986 | Coulter et al. .................. 141/1 |
| 5,959,221 | A | | 9/1999 | Boyd et al. ............. 73/864.24 |
| 6,074,617 | A | * | 6/2000 | DeYoung et al. ............ 422/104 |

FOREIGN PATENT DOCUMENTS

| EP | 0738541 | 10/1996 |
| EP | 1518605 | 3/2005 |

OTHER PUBLICATIONS

Supplementary European Search Report and Annex to the European Search Report on European Patent Application No. EP05753671 Dated Apr. 12, 2009.

* cited by examiner

*Primary Examiner*—Brian J Sines

(57) ABSTRACT

An indicator for enabling an analytical instrument to positively detect the presence of a vial in respective vial-receiving rack position regardless of whether the vial is oriented in a manner necessary for a code reader to read a code printed on the vial. Translation of a leaf spring upon insertion of a vial into a rack position causes a flag to obscure a code provided adjacent the rack position. An instrument into which the rack is installed interprets the failure of the code reader to detect this code as positive indication that a vial is disposed within the respective rack position.

6 Claims, 8 Drawing Sheets

VIAL PRESENCE INDICATOR FOR VIAL-BEARING RACK

CROSS REFERENCE TO RELATED APPLICATIONS

This application claims priority to U.S. Prov. Appl. No. 60/574,000, filed May 24, 2004, the entirety of which is hereby incorporated by reference.

STATEMENT REGARDING FEDERALLY SPONSORED RESEARCH OR DEVELOPMENT

N/A

BACKGROUND OF THE INVENTION

Accuracy and efficiency are fundamental requirements of automated laboratory analytical instruments. The requirement for a high degree of accuracy follows from the importance of the executed tests in patient diagnosis and treatment. The requirement for efficiency follows from the importance of timely results in patient care. In addition, a single, high-throughput instrument may obviate the need for multiple lower-efficiency instruments, thus leading to the potential for lower capital costs.

Modern automated analytical instruments often employ racks having one or two-dimensional arrays of vial-receiving positions for enabling the presentation of patient sample-bearing vials to the instrument. Optically readable codes, such as bar codes, are typically employed on both the racks and the individual vials. For instance, one code may be disposed upon a rack for uniquely identifying the rack to the instrument. Another code may be disposed on an outer surface of each patient sample vial to provide data such as patient identity, sample characterization, assays to be performed, etc. Yet another code may be provided adjacent or otherwise in association with each vial-receiving position on a rack to enable the creation of a logical association between the patient sample-bearing vial installed therein and its specific position on the respective rack.

To facilitate the reading of the vial-specific codes, each rack position is typically provided with a slot or other aperture through which the vial code may be viewed by the code reading device, which in the case of bar codes is a bar code scanner. Operators must ensure that each vial is oriented in the respective rack position such that the code located on the vial is viewable by the code reading device. Another alternative includes the provision of codes on labels spanning a majority of the circumference of each vial. Yet another option includes the use of vials having a physical feature that requires the vial to be properly oriented upon installation into the respective rack position.

Each of these options has a deficiency. If an operator does not properly orient a vial to present a code through a viewable aperture, the instrument may not recognize the presence of the vial, thus delaying performance of necessary assays until the positioning error is detected by the operator. The use of a custom-coded label raises costs and presents the possibility of inconsistency in code formats. Finally, the requirement of unique physical features on vials raises costs and obviates the use of laboratory standard vials.

Another approach to enabling an analytical instrument to confirm the presence of a vial in a rack position has been to print a code on a back wall of each position. Once a vial has been inserted in the position, the vial, its label, and its contents are intended to obscure the code. If the code reader cannot detect the back wall code for that position, the instrument assumes a vial is present. However, operator misalignment of the vial label may provide the opportunity for the code reader to detect the code, particularly if the vial and patient sample are transparent.

What is required is a means by which an analytical instrument can positively detect the presence of a vial in a rack position even if the vial coded label is improperly oriented with respect to the code reader.

BRIEF SUMMARY OF THE INVENTION

The presently disclosed invention overcomes the deficiencies associated with the prior art by enabling an automated laboratory analytical instrument to positively detect the presence in a rack of a vial and/or the vial label in a respective vial-receiving position regardless of whether the vial is oriented in a manner necessary for a code reader to read a code printed thereon or applied thereto.

In the prior art, racks typically provide each vial-receiving position with a positioning member which serves to properly position a vial. The importance of such positioning follows from the typical use of a robotic aspirating probe in analytical instruments; if a vial is out of position, a collision between the vial and the aspirating probe could occur. These positioning members also serve to prevent vials from jostling within the respective positions and spilling their contents.

One such positioning member frequently found in prior art vial-bearing racks is a leaf spring attached at one end to the rack. The presently disclosed invention utilizes the translation of a portion of a leaf spring or similar resilient, deformable member resulting from installation of a vial into a respective rack position to obscure a further code provided adjacent the rack position. The analytical instrument is configured to interpret the failure of the code reader to detect this code as a positive indication that a vial is disposed within the respective rack position.

In one embodiment, a leaf spring is adapted to form part of a compound positioning and annunciating structure. One end of the leaf spring is configured for being affixed to a rack adjacent a respective vial position. The opposite end of the leaf spring is configured to interfere with a pivoting arm which carries a code-obscuring flag at a distal end thereof. When a vial is inserted into the respective rack position, the free end of the leaf spring interferes with the pivoting arm, thereby positioning the flag over the respective code.

While the fundamental concept behind the presently disclosed invention can be represented by a number of embodiments, the underlying principle is the use of a deformable member, actuated upon container insertion, for positively representing to an automated analytical instrument that the container occupies a particular container-receiving position within the respective rack.

Other features, aspects and advantages of the above-described method and system will be apparent from the detailed description of the invention that follows.

BRIEF DESCRIPTION OF THE SEVERAL VIEWS OF THE DRAWINGS

The invention will be more fully understood by reference to the following detailed description of the invention in conjunction with the drawings of which.

DETAILED DESCRIPTION OF THE INVENTION

Figure 1:
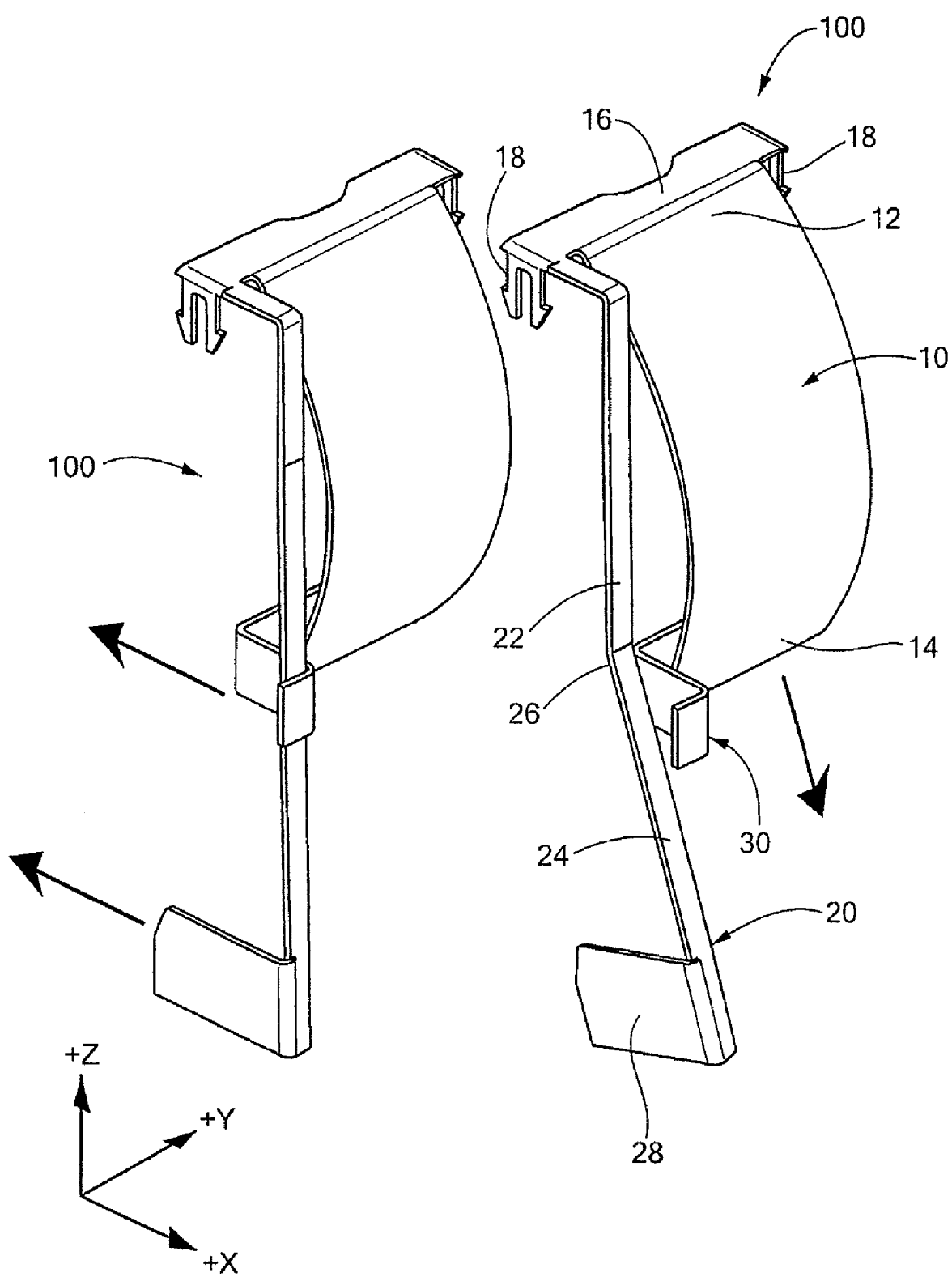
FIG. 1 is a top perspective view of a first embodiment of a vial presence indicator for a vial-bearing rack in both vial present and vial absent orientations.

A first embodiment of a vial presence indicator 100 for use with a vial-bearing rack is illustrated in FIG. 1 in both a vial installed orientation (left) and vial absent orientation (right). For the sake of simplicity, reference numerals are provided with respect to the right-hand illustration only.

The indicator 100 is mainly comprised of two portions: a leaf spring member 10 and a pivoting arm member 20, both of which are attached to or extend from the rack at a common end thereof. Two deformable engagement members 18 are utilized in the illustrated embodiment to affix a top bracket 16 of the indicator to the rack. With respect to the leaf spring member 10, an upper end 12 is attached to or integral with the bracket 16 while a lower end 14 is free to travel down (−Z) and in (−X) in response to the insertion of a vial into the respective vial position.

Also extending from or integral with the top bracket 16 is the pivoting arm member 20. As shown in the vial absent orientation on the right of FIG. 1, the arm member 20 is comprised of an upper arm segment 22 and a lower arm segment 24 which meet at a hinge point 26. A flag member 28 is affixed to the distal end of the lower arm segment 24 and generally extends from the lower arm segment in the −X direction.

Affixed to and projecting from the leaf spring lower end 14, adjacent the pivoting arm member 20, is a deflection bracket 30. As shown, in a first embodiment, the deflection bracket 30 has a first portion substantially parallel to and affixed to the leaf spring lower end. The first portion projects from the leaf spring lower end in the −Y direction. A second portion of the deflection bracket extends from the first portion in the +X direction. A third portion of the deflection bracket extends from the second portion in the −Y direction and, when in the vial absent orientation, extends in front of the lower arm segment 24.

Once a vial is inserted into the respective rack position, the leaf spring lower portion 14 is deflected down (−Z) and in (−X). This movement brings the deflection bracket 30 into contact with the lower arm segment 24, driving the lower arm segment in an arc about the hinge point 26 generally in the −X direction, which ultimately positions the flag member 28 over a respective code located on the rack, obscuring the code from a code reader. By not detecting this code, the analytical instrument recognizes the presence of a vial in the respective position.

Figure 2A:
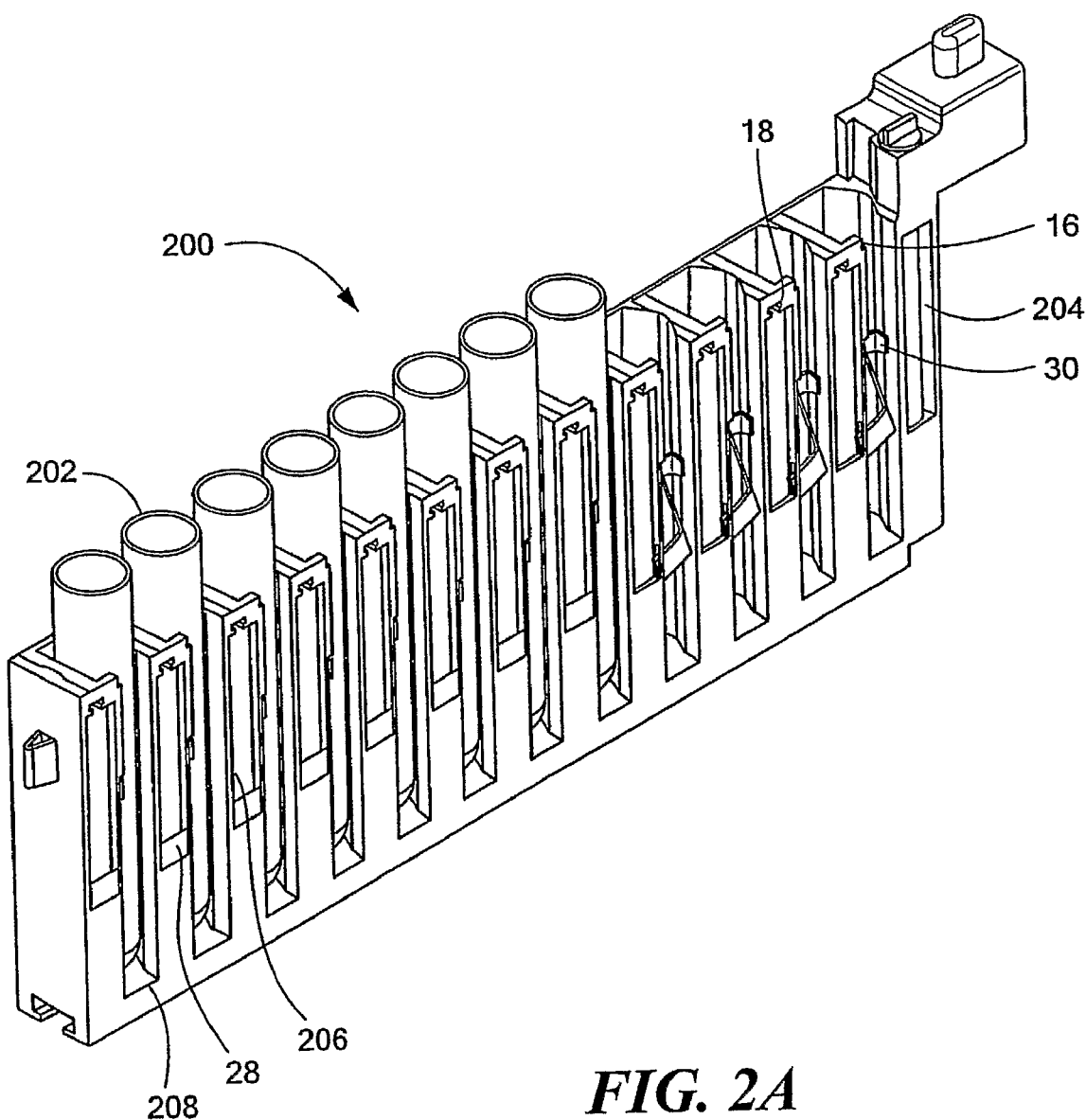
FIG. 2A is a top perspective view of a vial-bearing rack for tall vials incorporating the vial presence indicator of FIG. 1.
Figure 3A:
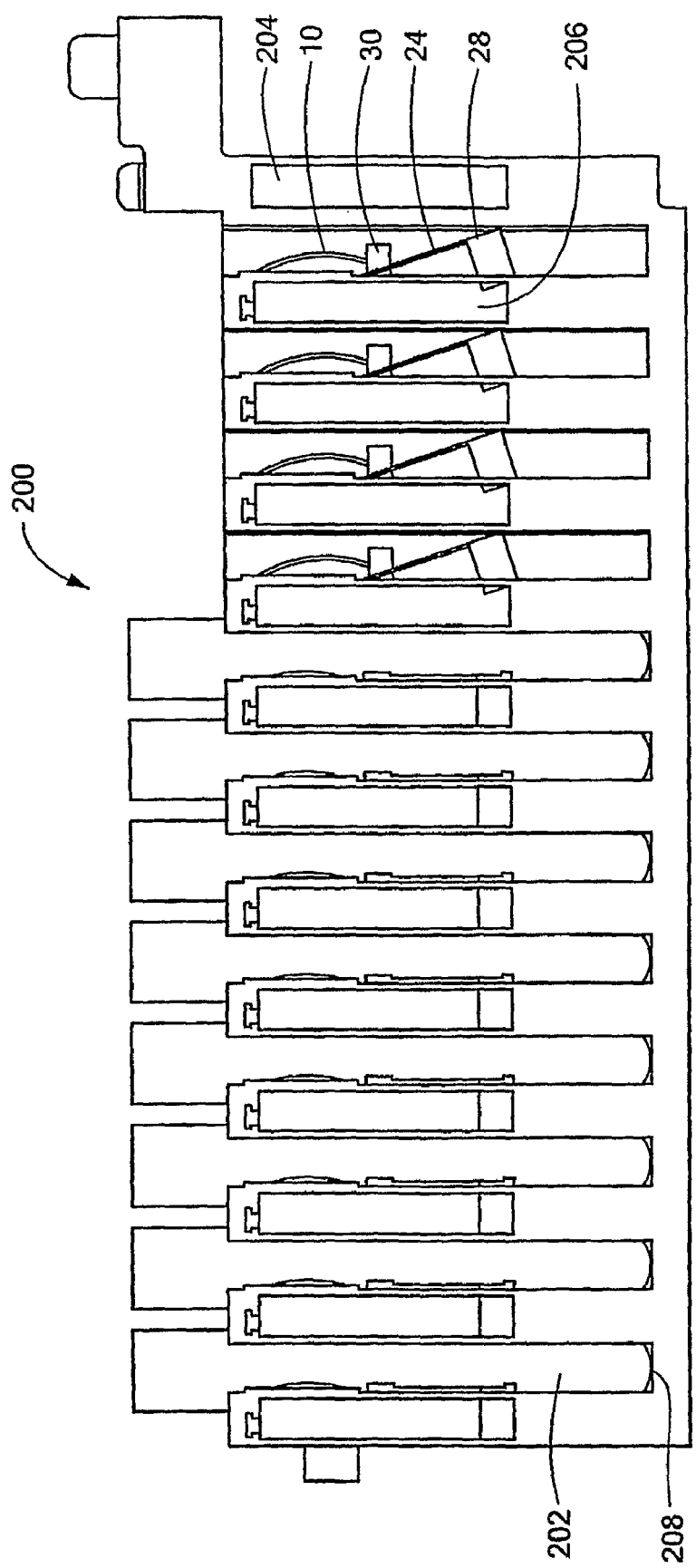
FIG. 3A is an elevation view of a vial-bearing rack for tall vials incorporating the vial presence indicator of FIG. 1.
Figure 4A:
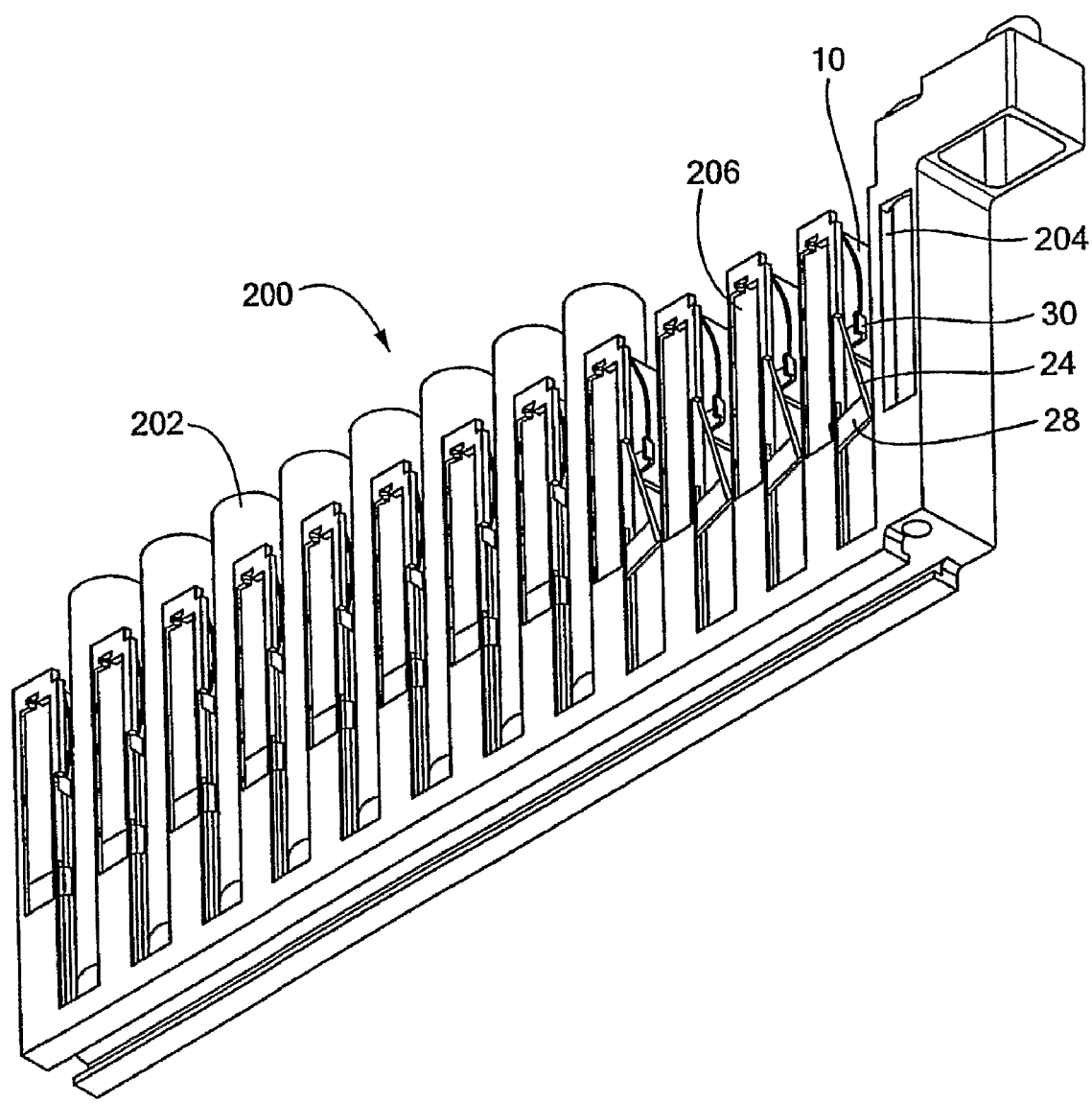
FIG. 4A is a bottom perspective view of a vial-bearing rack for tall vials incorporating the vial presence indicator of FIG. 1.

FIGS. 2A, 3A and 4A illustrate a first embodiment of a vial-bearing rack 200 employing the indicator 100 of FIG. 1. Eight vials 202 are installed in respective vial positions in this illustration, while four vial positions are shown unoccupied. Preferably, a rack-specific code 204 is provided to enable the analytical instrument in which it is installed to track the rack and the vials disposed therein. The code 204 may also generally characterize the constituent vials, such as by identifying the size or capacity of the vials. Specific rack aspects such as handles, rail following guide, and positioning members are not of significance to the presently disclosed invention. Thus, the rack 200 of FIGS. 2A, 3A, and 4A is merely one of many rack configurations which can benefit from the vial presence indicator 100.

It is envisaged that the rack used in conjunction with the presently disclosed indicator 100 has an opening in the wall of each vial-receiving position to enable a code disposed upon an installed vial to be read by a code reader. Preferably, each vial-receiving position is provided with an adjacent code 206 that positively identifies the respective position within the rack. In this manner, the analytical instrument can establish which vial is installed in each position on a given rack.

The position-specific code 206 may comprise two portions, a position identifying portion as described above and a position unoccupied portion. Alternatively, the position-specific code 206 may be discrete from a separate position unoccupied code. Either way, the indicator 100 does not interact with the position identifying portion but is configured to interact with the position unoccupied code. As shown in FIGS. 2A, 3A and 4A, each installed vial 202 has caused the respective flag 28 to obscure the lower portion of the respective position-specific code 206, which is the position unoccupied portion. The upper position identifying portion is never obscured by the indicator 100. With respect to the four unoccupied positions, the lower extent of the position-specific code 206 is readable by the code reader and indicates the absence of a vial in the respective position.

Figure 2B:
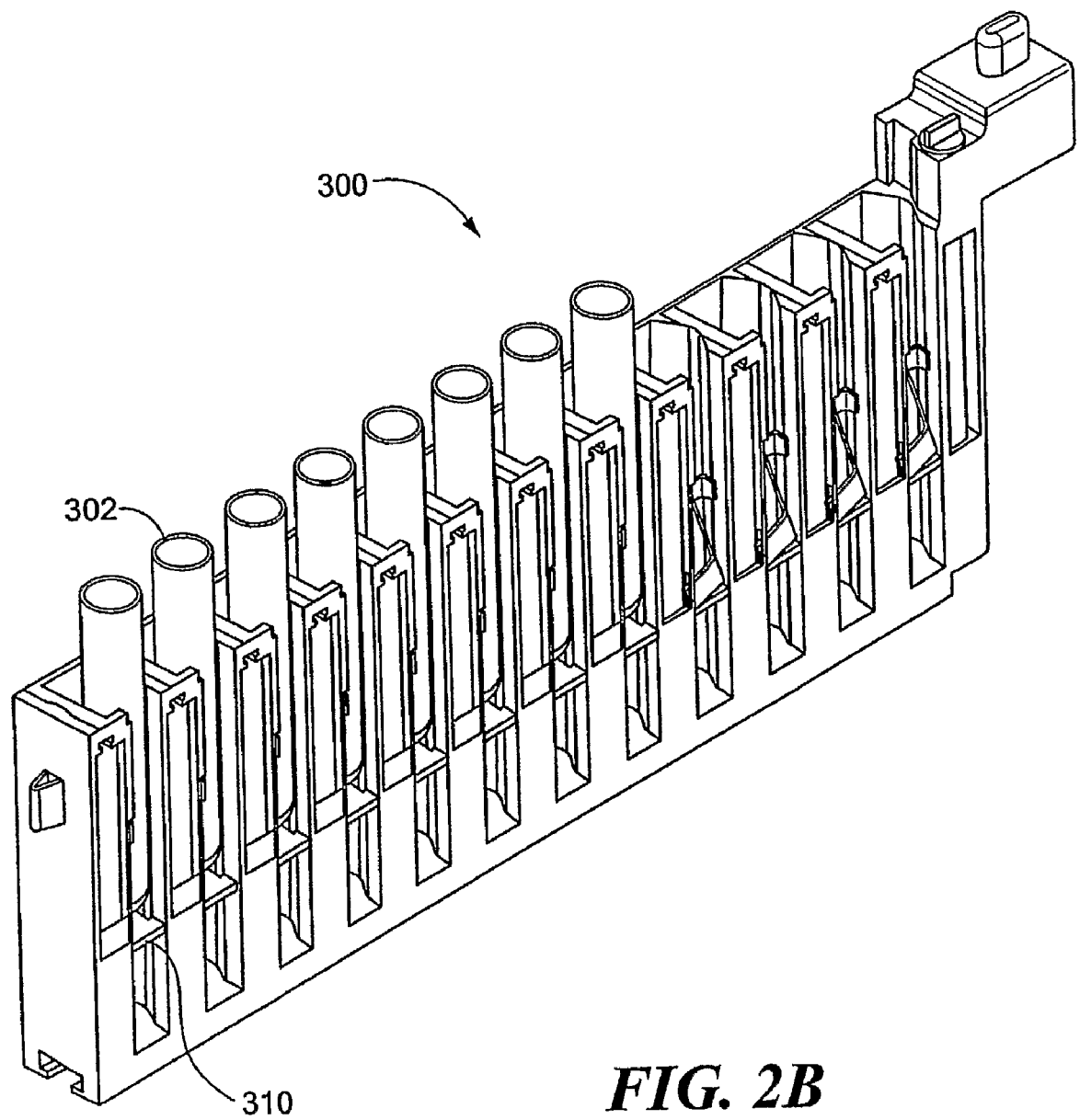
FIG. 2B is a top perspective view of a vial-bearing rack for short vials incorporating the vial presence indicator of FIG. 1.
Figure 3B:
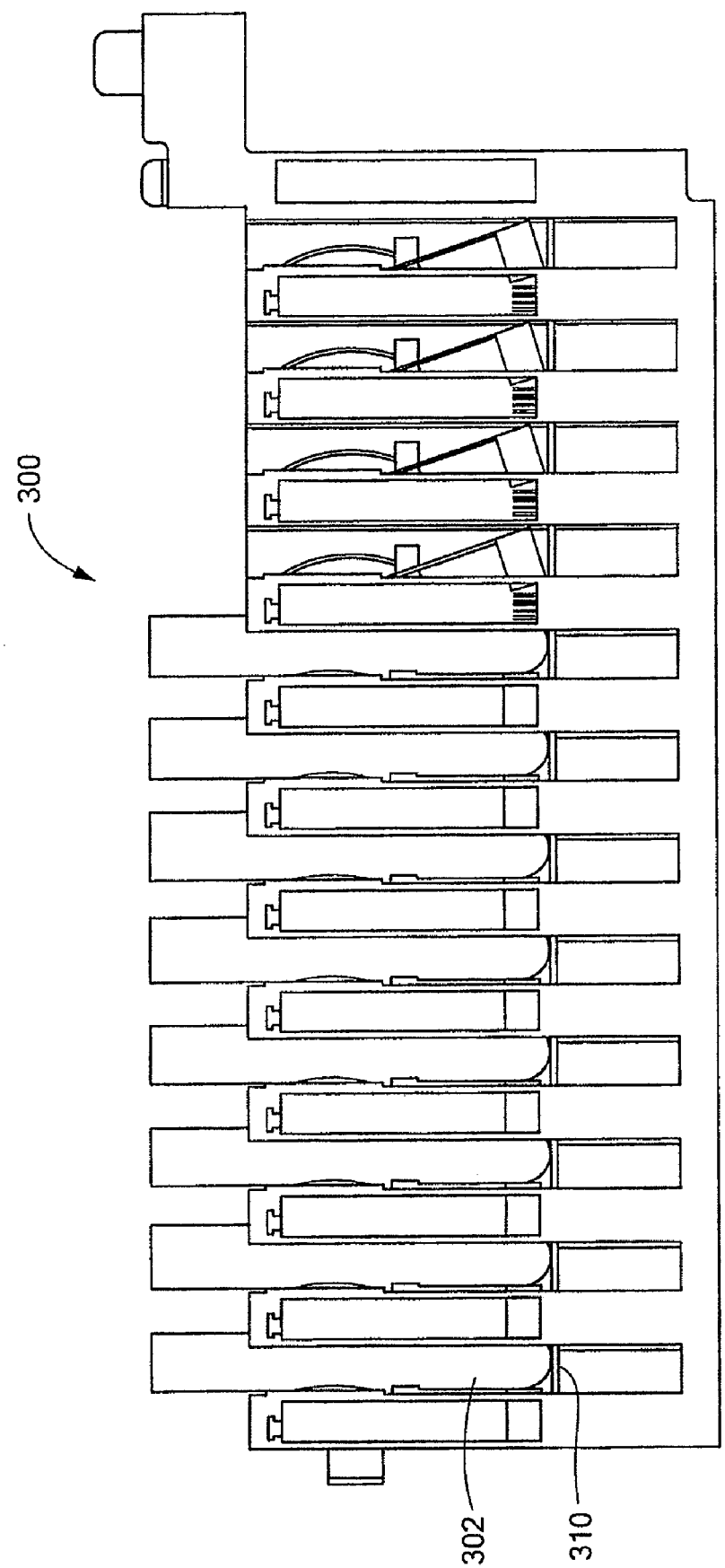
FIG. 3B is an elevation view of a vial-bearing rack for short vials incorporating the vial presence indicator of FIG. 1.
Figure 4B:
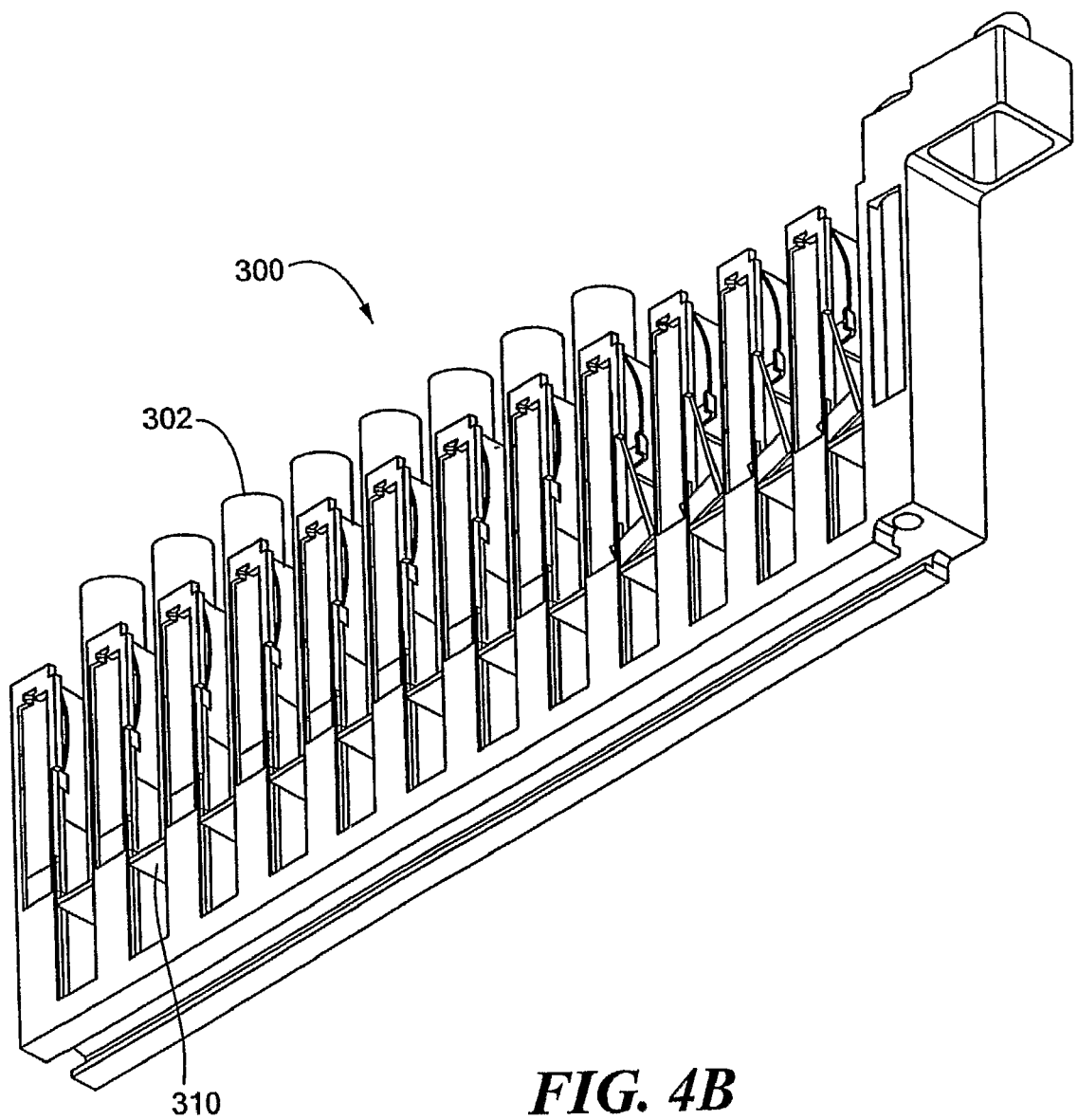
FIG. 4B is a bottom perspective view of a vial-bearing rack for short vials incorporating the vial presence indicator of FIG. 1.

The rack 300 of FIGS. 2B, 3B, and 4B are essentially identical to the rack 200 of FIGS. 2A, 3A, and 4A except for the relative position of a vial position floor. In the former, the rack 300 is provided with an adapter which provides a shallow floor surface 310 for shorter vials. The latter rack 200 does not employ such an adapter such that each vial-receiving position provides a deep floor surface 208. Preferably, the rack-specific code 204 identifies this characteristic. In either case, the indicator 100 is configured to not interfere with the vial position floor 208, 210.

Figure 5:
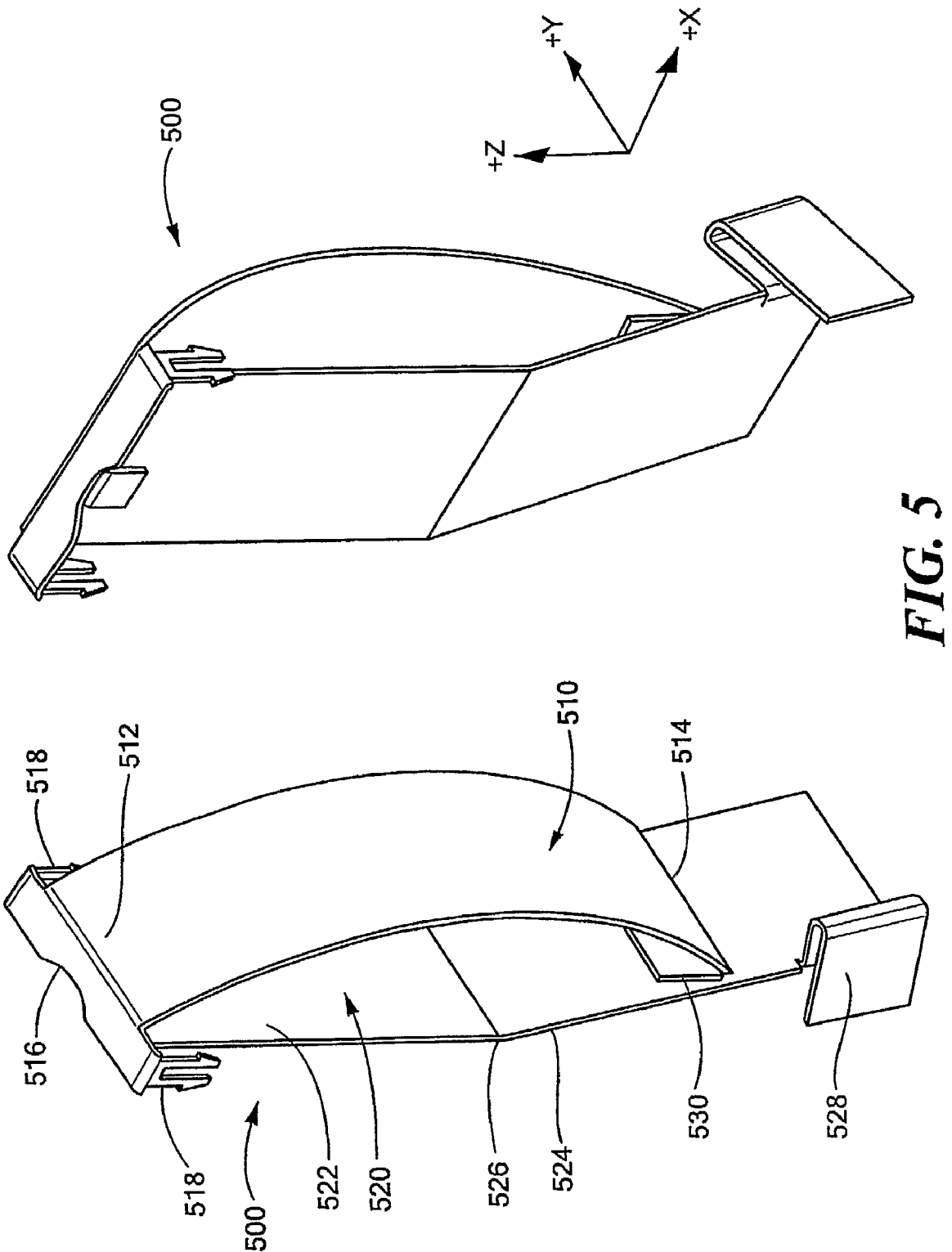
FIG. 5 is a top perspective view of an alternative embodiment of a vial presence indicator for a vial-bearing rack.

An alternative indicator embodiment 500 is illustrated in FIG. 5. Here, the leaf spring member 510 with upper and lower ends 512, 514, top bracket 516, and deformable engagement members 518 are substantially similar to the embodiment of FIG. 1 except that the leaf spring lower end 514 has an upward terminating edge 530 instead of a deflection bracket 30. The pivoting arm member 20 of FIG. 1 is replaced with a deflecting planar member 520 in FIG. 5. As with the arm member of FIG. 1, the planar member has upper and lower segments 522, 524 separated by a hinge point 526. With no vial installed in a respective vial-receiving position, the lower planar segment 524 is deflected in the +X direction. Once a vial is installed, the terminating edge 530 slides down (−Z) and in (−X), thus forcing the lower planar segment 524 to move substantially in the −x direction. A flag member 528, attached to the lower extent of the planar lower segment, thus obscures an unoccupied code disposed on the rack adjacent the respective vial-receiving position.

A number of alternative embodiments may be identified. For example, the indicators have been recited as being operable in conjunction with vial-receiving positions in vial-bearing racks, though the concept can be easily adapted to a variety of three-dimensional objects such as test tubes, cartridges, work-in-process objects, etc. Preferably, such objects have a continuous outer surface which can be brought into contact with the leaf spring of the indicator, thereby urging the flag over a respective unoccupied code.

The various portions of the indicators 100, 500 may be provided of various materials, depending upon the intended application, including metal and/or plastic. Additionally, the various parts may be formed as a unitary structure or assembled from a number of discrete pieces. Assembly may be achieved by any of various known techniques, such as heat tacking, welding, gluing, interference fit, or mechanical fasteners. The indicators may be attached to a rack, such as via the deformable engagement members 18, 518 or any similar structure(s), or may be integrally formed with the rack.

While in the context of a laboratory analytical instrument it is preferable to provide a discontinuity along each vial-receiving position to enable a code reader to detect a code disposed upon a respective vial, other contexts may prefer or require that the vial-receiving position be substantially enclosed. This may be the case if the vials or other objects contain temperature or light sensitive materials. In this case, the indicator flag may be configured to pass within an aperture in rack adjacent the respective vial-receiving position. For instance, the flag 528 of FIG. 5 could be used for this purpose.

Having described preferred embodiments of the presently disclosed invention, it should be apparent to those of ordinary skill in the art that other embodiments and variations incorporating these concepts may be implemented. Accordingly, the invention should not be viewed as limited to the described embodiments but rather should be limited solely by the scope and spirit of the appended claims.

What is claimed is:

1. A container presence indicator for a container carrier having a container receptacle and an optically-readable code corresponding to the container receptacle, comprising:

a first deformable member disposed within the container receptacle;

a second deformable member disposed within the container receptacle and adjacent the first deformable member, the first deformable member configured to, upon deformation, interfere with and to deform the second deformable member; and a flag member configured to project from the second deformable member adjacent the optically-readable code, whereby installation of the container into the container receptacle interferes with and deforms the first deformable member in a first direction, which is configured to interfere with and to deform the second deformable member in a second, orthogonal or substantially orthogonal direction, which disposes the flag member substantially over the optically-readable code, to prevent said code from being read by an optical reader.

2. The indicator of claim 1, wherein the first deformable member is a leaf spring.

3. The indicator of claim 1, wherein the first deformable member comprises a deflection bracket for interfering with the second deformable member upon installation of the container.

4. The indicator of claim 1, wherein the second deformable member comprises a pivoting arm member comprised of a stationary portion, a radially translatable portion, and a hinge member therebetween.

5. The indicator of claim 4, wherein the first deformable member, upon deformation, interferes with and deflects the radially translatable portion of the second deformable member.

6. The indicator of claim 5, wherein the flag member projects from the radially translatable portion at a distal end thereof, whereby installation of the container results in the flag member being disposed substantially over the container absence code.

* * * * *